(12) United States Patent
Taniike et al.

(10) Patent No.: US 7,238,160 B2
(45) Date of Patent: Jul. 3, 2007

(54) APPARATUS FOR MEASURING BIOLOGICAL COMPONENT

(75) Inventors: Yuko Taniike, Osaka (JP); Mariko Miyashita, Nishinomiya (JP); Shin Ikeda, Katano (JP); Toshihiko Yoshioka, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 386 days.

(21) Appl. No.: 10/512,939

(22) PCT Filed: Jan. 16, 2004

(86) PCT No.: PCT/JP2004/000286

§ 371 (c)(1),
(2), (4) Date: Nov. 1, 2004

(87) PCT Pub. No.: WO2004/064635

PCT Pub. Date: Aug. 5, 2004

(65) Prior Publication Data

US 2005/0159678 A1    Jul. 21, 2005

(30) Foreign Application Priority Data

Jan. 17, 2003    (JP)    ............................. 2003-009461

(51) Int. Cl.
    *A61B 5/00*    (2006.01)
(52) U.S. Cl. .................................................. 600/583
(58) Field of Classification Search ................ 600/573, 600/578, 583, 584; 606/181–185; 604/164.06; 422/58; 204/403.01, 403.02, 403.03; 435/7.1; 702/19

See application file for complete search history.

(56) References Cited

U.S. PATENT DOCUMENTS 6,349,229 B1    2/2002    Watanabe et al.

(Continued)

FOREIGN PATENT DOCUMENTS

CN    1263448 A    8/2000

(Continued)

OTHER PUBLICATIONS

"Biosensor", edited by Shuichi Suzuki, Kodansha, Mar. 1984, pp. 100-101.

(Continued)

*Primary Examiner*—Max Hindenburg
*Assistant Examiner*—Brian Szmal
(74) *Attorney, Agent, or Firm*—Wenderoth, Lind & Ponack, L.L.P.

(57)    ABSTRACT

The present invention relates to a biological component measurement apparatus set, in which a puncture mechanism for puncturing skin of a subject to collect a sample blood is integrated with a biosensor measurement apparatus. The puncture mechanism includes a puncture needle, and a cap which is detachably engaged with a body of the apparatus, wherein the cap has a skin contact surface which is brought into contact with the skin for puncturing. The skin contact surface having an opening through which the puncture needle moves to puncture the skin, and is shaped so as to fit a surface shape of the skin to be punctured. The set includes a plurality of different caps each corresponding to a different sample collection site so that a plurality of different sample collection sites can be selected.

16 Claims, 11 Drawing Sheets

U.S. PATENT DOCUMENTS

| | | | |
|---|---|---|---|
| 6,706,049 B2 * | 3/2004 | Moerman | 606/181 |
| 6,706,159 B2 * | 3/2004 | Moerman et al. | 204/403.03 |
| 2003/0175806 A1 * | 9/2003 | Rule et al. | 435/7.1 |
| 2003/0223906 A1 * | 12/2003 | McAllister et al. | 422/58 |

FOREIGN PATENT DOCUMENTS

| | | |
|---|---|---|
| JP | 63-283625 | 11/1988 |
| JP | 3-202764 | 9/1991 |
| JP | 2001-346781 | 12/2001 |

OTHER PUBLICATIONS

John M. Ellison et al., "Rapid Changes in Postprandial Blood Glucose Produce Concentration Differences at Finger Forearm, and Thigh Sampling Sites", Diabetes Care vol. 25, No. 6, Jun. 2002, pp. 961-964.

* cited by examiner

APPARATUS FOR MEASURING BIOLOGICAL COMPONENT

BACKGROUND OF THE INVENTION

1. Field of the invention

The present invention relates to a measurement apparatus and a measurement method for measuring a specific biological component in a biological sample collected by puncturing a living body. Specifically, the present invention relates to a biological component measurement method and apparatus for storing, processing, and/or displayed measurement values in association with a sample collection site.

2. Description of the Related Art

Up to now, various types of biosensors utilizing specific catalytic actions of enzymes have been developed. Specifically, glucose sensors for quantifying glucose are widely used for measurements of blood glucose levels (glucose concentrations in blood) in clinical examinations. Hereinafter, the glucose sensors will be discussed as an example of the biosensors.

As a method for electrochemically quantifying glucose, a method that utilizes glucose oxidase (EC1.1.3.4; hereinafter abbreviated as GOD), which is an enzyme, and an oxygen electrode or a hydrogen peroxide electrode is generally known (e.g., "BIOSENSOR" edited by Shuichi Suzuki, KODANSHA, March 1984, pp. 100-101).

Although this method accurately quantifies glucose in a biological sample by making use of the specificity of an enzyme reaction, it has a disadvantage that measurement results are affected by oxygen concentration within the sample. If there is no oxygen in the sample, no measurements can be performed.

Accordingly, there have been developed glucose sensors of a new type that does not utilize, as an electron carrier, oxygen but utilizes organic compounds such as potassium ferricyanide, ferrocene derivatives, quinone derivatives and so on, or metal complexes.

By utilizing the organic compound or the metal complex as an electron carrier, glucose can be accurately quantified without being affected by the oxygen concentration in a biological sample.

In addition, in this case, a reagent layer containing an enzyme and an electron carrier can be integrated with an electrode system under almost dry conditions, and therefore, it is possible to produce disposable glucose sensors based on this technology, and such glucose sensors have recently come into widespread use.

As for a disposable glucose sensor, glucose can be readily measured with a measurement apparatus by merely introducing a biological sample into the sensor that is detachably connected to the measurement apparatus (see, for example, Japanese Laid-open Patent Publication No. 03-202764).

The widespread use of the glucose sensors such as the above has made it possible for patients with diabetes to readily measure their blood glucose levels at home. As the procedure, a method as described below is common.

Initially, a collection site is punctured by means of a needle attached to a puncture apparatus. Then, a biological sample (i.e., blood) is squeezed out from the punctured site. Finally, a sensor, which has been previously attached to a measurement apparatus, is brought close to the punctured site so as to cause a biological sample supply opening of the sensor to be in contact with the squeezed blood, thereby supplying the blood into a sample chamber of the sensor. The biosensor detects glucose in the blood thereby quantifying the amount of glucose contained in the blood. Regarding measurements using a glucose sensor as described above, a substrate concentration in a biological sample can be readily measured using a biological sample in an amount of the order of a few µl.

When measuring blood glucose levels, conventionally, it is common to collect blood by puncturing a fingertip. However, in recent years, a method, which collects blood from, for example, a forearm rather than a fingertip, to measure blood glucose levels has come into use.

This method is advantageous in, for example, that no scar remains in fingertips after puncturing, and the puncture is less painful because forearms are not as sensitive as fingertips. Thus, diabetes patients are provided with more options for measuring their own blood glucose levels.

Recently, with intent to further simplify the measurement procedure, products that combine a puncture apparatus and a measurement apparatus for glucose sensors have become commercially available. These products have an advantage that puncturing by the puncture apparatus and measurement by the sensor can be performed with a single measurement apparatus, whereby it is possible to reduce the number of measurement steps that a patient with diabetes has to go through.

An example of such a conventional combined measurement apparatus is a biosensor measurement apparatus (SofTact™) for measuring glucose at levels from a forearms, which is currently commercially available from Abbott Laboratories. FIG. 11 shows a schematic diagram thereof.

As shown, a measurement apparatus 91, which has attached thereto a biosensor for measuring glucose in blood and a puncturing member for puncturing a living body, includes a switch 93 for starting a measurement, a display member 92 for displaying obtained results, and a contact surface 96 for contact with a living body. Contact surface 96 includes a collection opening 97 through which the puncturing member protrudes to collect blood extracted from a living body. The biosensor apparatus of this configuration is designed such that the contact surface for contact with the living body fits a forearm, and therefore, it is difficult to collect samples from another location (e.g., a fingertip).

On the other hand, it has been reported that when the concentration of glucose in the blood varies largely, for example, immediately after a meal, measurement values of glucose concentrations obtained by biosensors vary among different blood collection sites (for example, a fingertip, a forearm, a thigh, etc.) even in the same subject (e.g., John M. ELLISON, Diabetes Care Vol. 25, No. 6, 961-964, (2002)). Therefore, even with the same subject, depending on the elapsed time after the meal, there may occur a problem where an actual measurement value of a sample collected from a forearm, for example, cannot be compared directly with standard values based on samples collected from a fingertip.

SUMMARY OF THE INVENTION

As such, in the case of measuring, for example, blood glucose especially after a meal when the blood glucose fluctuates largely, measured blood glucose values often vary between the blood collections sites. However, there is no conventional measurement apparatus which has a mechanism for distinguishing between measurement values obtained from blood samples collected at different sites (e.g., a value of blood glucose from a blood sample collected from a forearm and a value of blood glucose from a blood sample collected from a fingertip).

Furthermore, the above-described conventional measurement apparatus integrated with a puncture apparatus has a disadvantage in that a biological sample collection site is limited to a forearm due to the design of a contact surface intended to be in contact with the sample collection site.

To solve the above conventional problems, the present invention aims to provide a biological component measurement apparatus capable of carrying out measurements both at a fingertip and at any sites other than the fingertip, without limiting the sample collection site.

Furthermore, the present invention aims to provide a biological component measurement apparatus that comprises, in one apparatus, a mechanism that stores, processes, and/or displays measurement values in association with their respective sample collection sites. Specifically, the present invention aims to provide a biological component measurement apparatus that comprises a mechanism for correcting a value of blood glucose of a sample collected from a site other than a fingertip based on the sample collection site and sampling time.

Still further, the present invention aims to provide a biological component measurement apparatus including a puncture apparatus integrated with a biosensor apparatus capable of carrying out measurements both at a fingertip and at any sites other than the fingertip, storing, processing, and/or displaying measurement results in association with the sample collection sites, without limiting the sample collection site.

Still further, the present invention aims to provide a biological component measurement apparatus capable of storing, processing, and/or displaying measurement results in association with their respective sample collection sites such that accurate monitoring and patient treatment can be provided, even in the above case where the blood glucose values are monitored with time, using a measurement device capable of collecting samples not only from a fingertip but also from sites other than the fingertip, including a forearm, a thigh, etc. Specifically, the present invention aims to provide a biological component measurement apparatus, which comprises a mechanism that corrects a blood glucose value of a sample collected from a site other than a fingertip for fluctuations with the sampling site and sampling time.

To achieve the above-described objects, a first aspect of the present invention provides a biological component measurement apparatus set, in which a puncture mechanism for puncturing skin of a subject to collect a sample blood is integrated with a biosensor measurement apparatus. In this biological component measurement apparatus set, the puncture mechanism comprises at least a puncture needle and a cap which is detachably engaged with a body of the apparatus. The cap has a skin contact surface which is brought into contact with the skin for puncturing, the skin contact surface having an opening through which the puncture needle moves to puncture the skin, and being shaped so as to fit a surface shape of the skin to be punctured. This biological component measurement apparatus set comprises a plurality of different such caps each corresponding to a different sample collection site so that a plurality of different sample collection sites can be selected.

In a preferred embodiment, the biological component measurement apparatus set of the present invention comprises a cap for collecting a sample from a fingertip and a cap for collecting a sample from a forearm. In another embodiment, a cap for collecting a sample from any site selected from the group consisting of a palm, an upper arm, a thigh, and an abdomen is further included.

In a further preferred embodiment of the biological component measurement apparatus set of the present invention, the biosensor measurement apparatus comprises: a biological component information input member (device) for entering measurement information from the biosensor, wherein the biological component information input member comprises a biosensor attachment member, a sample collection site input member for entering information about the sample collection site, a memory member (device) a computing member (device) for calculating a substrate concentration in the sample of blood based on the information from the biological component information input member, and a display member (device) for displaying the calculated substrate concentration, wherein the entered information about the sample collection site is stored in the memory member together with the calculated substrate concentration.

In a preferred embodiment of the biological component measurement apparatus set of the present invention, the biosensor is a glucose sensor.

In a further preferred embodiment of the biological component measurement apparatus of the present invention, the entered information about the sample collection sites is displayed on the display member together with the calculated substrate concentration.

In an another preferred embodiment of the biological component measurement apparatus of the present invention, the cap has a pair of electric contacts placed on at least a part of a portion engaged with the body of the apparatus, the contacts being electrically connected to a constant resistance specific to the cap. Further, the sample collection site input member comprises a resistance measurement device and a second pair of electric contacts electrically connected to the resistance measurement device, the second pair of electric contacts being brought into contact with the pair of electric contacts to form an electric circuit such that the resistance measurement device detects the constant resistance, when the cap is engaged with the body of the apparatus. In this embodiment, the sample collection site is recognized based on the detected value of the constant resistance.

In a additional preferred embodiment of the biological component measurement apparatus set of the present invention, the biosensor measurement apparatus further comprises a mealtime input member (device) for entering a mealtime or an elapsed time after a meal, and the memory member previously has stored therein a correction table or a correction equation for correcting measurement values based on the elapsed time after a meal and the sample collection site, and the computing member refers to the correction table or the correction equation stored in the memory member, and calculates a corrected substrate concentration based on the mealtime or the elapsed time after a meal entered in the mealtime input member and the sample collection site entered in the sample collection site input member.

The present invention also provides, in another aspect, a biological component measurement apparatus with which a puncture mechanism for puncturing skin of a subject to collect a sample blood is integrated. In this biological component measurement apparatus, the puncture mechanism comprises at least a puncture needle, and a cap which is detachably engaged with a body of the apparatus. This cap has a skin contact surface which is brought into contact with the skin for puncturing, the skin contact surface having an opening through which the puncture needle moves to puncture the skin. On the other hand, the biosensor measurement apparatus includes a biological component information input member for entering measurement information from the biosensor, wherein the biological component information input member comprises a biosensor attachment member, a sample collection site input member for entering information about the sample collection site, a computing member for calculating a substrate concentration in the sample blood based on the information from the biological component information input member, a memory member for storing the entered information about the sample collection site together with the calculated substrate concentration, and a display member for displaying the calculated substrate concentration. The biological component measurement apparatus of the present invention according to this embodiment is characterized in that the skin contact surface of the cap comprises at least two sensors for detecting a contact with skin, which is electrically connected to the sample collection site input member when the cap is engaged with the body of the apparatus, and the sample collection site input member recognizes the sample collection site based on the number and/or a combination of sensors which have detected contact with the skin.

In a preferred embodiment of the biological component measurement apparatus according to another aspect of the present invention, the sample collection site input member recognizes the sample collection site as a fingertip if only a part of the sensors detect contact with the skin.

In a further preferred embodiment of the biological component measurement apparatus according to another aspect of the present invention, the sample collection site input member recognizes the sample collection site as any site selected from the group consisting of a palm, a forearm, an upper arm, a thigh, and an abdomen, if all of the sensors detect contact with the skin.

In another preferred embodiment of the biological component apparatus according to another aspect of the present invention, the above biosensor measurement apparatus further comprises a mealtime input member for entering a mealtime or an elapsed time after a meal, and the memory including member previously has stored a correction table or a correction equation for correcting the measurement values based on the elapsed time after a meal and the sample collection site, and the computing member refers to the correction table or the correction equation stored in the memory member, and calculates a corrected substrate concentration based on the mealtime or the elapsed time after a meal entered in the mealtime input member and the sample collection site entered in the sample collection site input member.

The present invention provides, in still another aspect, a biosensor measurement apparatus. This biosensor measurement apparatus comprises a biological component information input member for entering measurement information from the biosensor, wherein the biological component information input member comprises a biosensor attachment member, a sample collection site input member for entering information about the sample collection site, a computing member for calculating a substrate concentration in the sample blood based on the information from the biological component information input member, a memory member for storing the entered information about the sample collection site together with the calculated substrate concentration, and a display member for displaying the calculated substrate concentration.

In a preferred embodiment of the biosensor measurement apparatus according to a still another aspect of the present invention, the biosensor measurement apparatus further comprises a mealtime input member for entering a mealtime or an elapsed time after a meal, the memory member previously has stored a correction table or a correction equation for correcting the measurement values based on the elapsed time after a meal and the sample collection site, the computing member refers to the correction table or the correction equation stored in the memory member, and calculates a corrected substrate concentration based on the mealtime or the elapsed time after a meal entered in the mealtime input member and the sample collection site entered in the sample collection site input member, the memory member further stores the corrected substrate concentration, and the display member displays the corrected substrate concentration.

The biological component measurement apparatus of the present invention associates measurement results with biological sample collection sites, thereby making it possible to more accurately interpret measurement values. Also, the present invention provides recognition of sampling sites to choose a method for correcting the measurement result, making it possible to carry out accurate measurements.

BRIEF DESCRIPTION OF THE DRAWINGS

FIG. 1A illustrates a state where the cap 18 is engaged with a housing 11; FIG. 1B illustrates a state where the cap 18 is disengaged.

DETAILED DESCRIPTION OF THE INVENTION

Figure 1A:
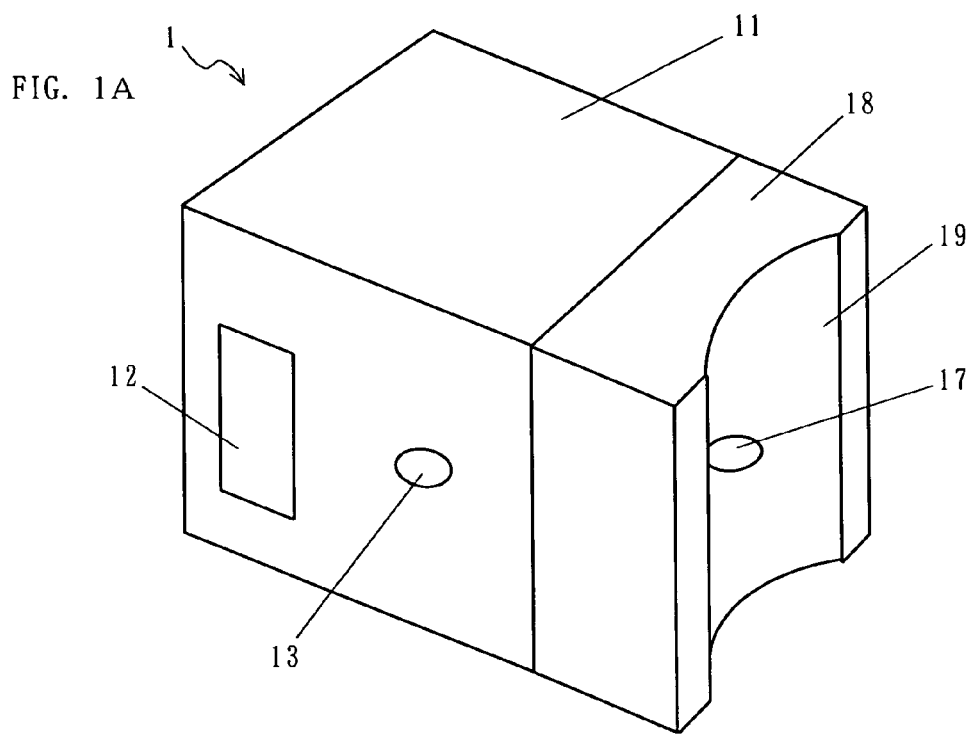
FIGS. 1A and 1B show schematic view illustrating an external appearance of a biological component measurement apparatus 1 integrated with a puncture apparatus in accordance with an embodiment of the present invention, including a cap 18 adapted to collect blood from a fingertip.

Hereinafter, embodiments of the present invention are specifically described referring to the drawings.

Note that in the following embodiments, a measurement apparatus and a measurement method for quantifying blood glucose levels are described as an example.

FIRST EMBODIMENT

Figure 1B:
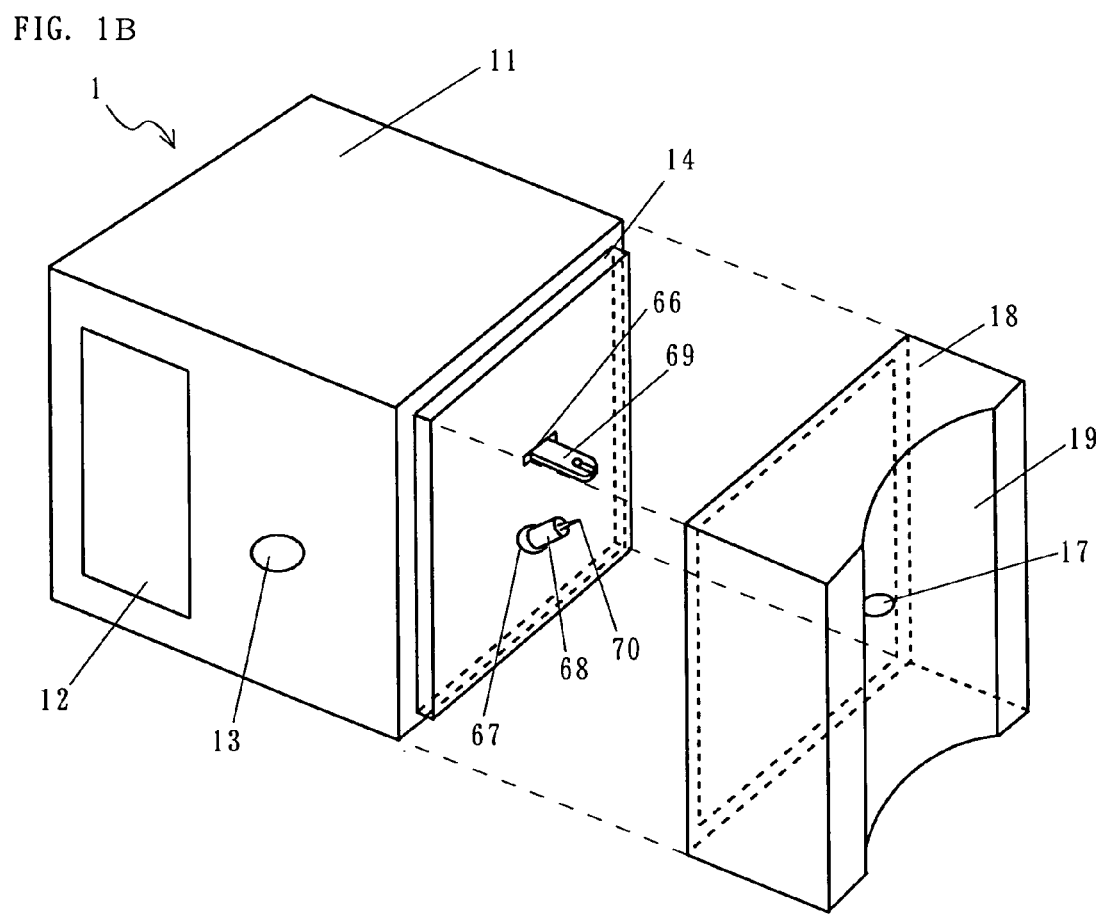
Figure 2:
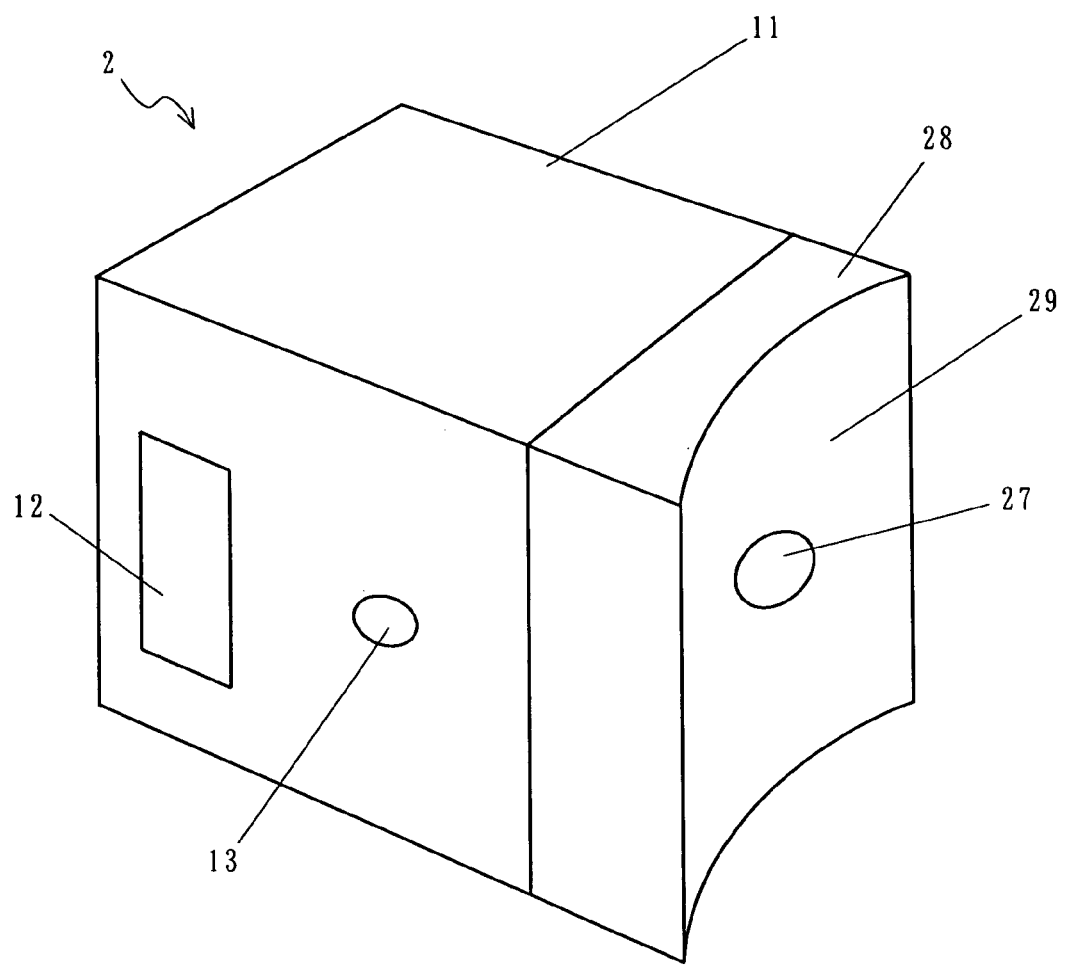
FIG. 2 is a schematic view illustrating an external appearance of a biological component measurement apparatus 2 integrated with a puncture apparatus in accordance with an embodiment of the present invention, including a cap 28 adapted to collect a biological sample from a forearm.

A first embodiment of the present invention is described referring to FIGS. 1A, 1B, and 2.

FIGS. 1A and 1B are a schematic view illustrating an external appearance of a biological component measurement apparatus 1 in accordance with the present invention, including a cap 18 adapted for collection of a biological sample (i.e., blood) from a fingertip, with a puncture apparatus being integrated into the measurement apparatus 1. FIG. 1A illustrates a state where the cap 18 is engaged with a housing 11 that houses a body of the apparatus and constitutes a part thereof. FIG. 1B illustrates a state where the cap 18 is disengaged.

The biological component measurement apparatus 1 includes the housing 11 and the cap 18 which are made of a material such as plastic. The housing 11 includes a display member 12, which is comprised of a liquid crystal display or the like, for displaying measurement values measured by a biosensor 69, and switch 13 for starting a measurement.

As shown in FIG. 1B, the housing (body) 11 includes a gasket 14 or an other sealing mechanism for sealing a portion for engagement with the cap 18. The cap 18 is detachably attached to the housing 11 by means of friction engagement, a detent or the like.

Provided in a portion of the housing 11 that is covered by the cap 18 when the cap 18 is engaged with the housing 11 are: a puncturing member attachment opening 67 for attaching a puncturing member that includes a puncture needle holder 68 and a puncture needle 70 and moves therethrough for puncturing skin to collect a biological sample; and a biosensor attachment opening 66 for attaching the biosensor 69 for measuring a biological component in the collected biological sample.

Provided in the housing 11 is an assembly (not shown) for allowing the above-described puncturing member to protrude through the puncturing member attachment opening 67. For such an assembly, a known assembly that utilizes air pressure, a spring or the like as described in Japanese Laid-open Patent Publication No. 2001-346781, for example, may be used. Further provided in the housing 11 are a vacuum pump, an electrical device, a battery, etc., (not shown) for operating the assembly as mentioned.

Still further provided in the housing 11 is a slot (or an attaching member) (not shown) for detachably attaching the biosensor 69 through the opening 66. Normally, the biosensor 69 is of a disposable type. The biosensor 69 includes one or more electric contacts (not shown) on an end portion that is inserted into the slot, so as to be in contact with one or more electric contacts (not shown) placed within the slot. Still further provided in the housing 11 are a CPU (not shown) for performing data processing, etc., which is connected to the electric contact as mentioned via an electric circuit, and a data storage member (not shown) consisting of a RAM, a ROM, an external memory device or the like.

The cap 18 includes a biological sample collection opening 17, providing a mechanism where, through this opening, the puncturing member including the puncture needle 70 that is attached to the needle holder 68 which is attached to opening 67 of the housing 11 protrudes, thereby puncturing skin of a subject. The surface at which the cap 18 is in contact with a living body, i.e., a living body contact portion 19, (i.e., skin contact surface), has a curved surface that fits a shape of each collection site. For example, the living body contact portion 19 of the cap 18 of FIGS. 1A and 1B is designed to a shape having a curved surface that fits well with a ball of the tip of a finger placed thereon.

When in use, the measurement apparatus 1 is placed such that the living body contact portion 19 is in close contact with the surface of skin of the sampling site of the subject from whom a biological sample is collected. In doing so, a seal made of an elastic body, such as rubber or elastomer, is preferably provided around the biological sample collection opening 17 such that the opening 17 is sealed in contact with the skin.

As illustrated, the switch 13 is normally composed of a push button or the like, and a measurement operation is started by pressing the button. Specifically, when the switch 13 is pressed, a stopper provided in the housing 11 for holding the puncturing member is released, and a mechanism, such as a spring, which is based on a mechanical energy, causes the puncturing member attached in the housing 11 to protrude, thereby puncturing a fingertip. Preferably, when the switch 13 is pressed, the above-described vacuum pump, the electric device, etc., (not shown) in the housing 11 are activated to draw a vacuum, thereby pulling out the skin surrounded by the opening 17 relative to the opening 17, so that the skin is engorged with blood, and the skin is punctured by the puncture needle provided to the puncturing member. Puncturing such as the above, is normally performed by activating a foresaid assembly for the puncturing member (not shown) after the lapse of an appropriate time period previously set by the electrical device loaded with a program.

After puncturing, the above-described slot to which the biosensor 69 is attached is moved towards the punctured skin thereby bringing the biosensor 69 into contact with blood from the fingertip to measure the concentration of the biological component (i.e., glucose). As the mechanism for moving the slot, a known sliding mechanism as described in, for example, Japanese Laid-open Patent Publication No. 2001-346781 may be used. Also, the start of movement of the slot may be interlocked with the end of the operation of the puncturing assembly. Note that it is not necessary to provide the slot moving mechanism in the measurement apparatus 1 as long as the positions of the slot and the biosensor 69 are previously set such that the oozed blood is brought into contact with the tip of the biosensor 69 attached to the slot.

The biosensor 69 includes, in the sample collection chamber which contacts the biological sample, at least a pair of electrodes and a reagent system supported upon the electrodes that includes glucose dehydrogenase, which specifically reacts with glucose in blood, and an electron carrier (not shown). Once the blood is introduced into the sample chamber of the biosensor, the reagent system reacts with glucose within the blood. While a measurement member (not shown) of the measurement apparatus 1 applies a voltage to the electrode system of the biosensor 69, a current value including any change of a current value due to the above reaction is measured by a biological component information input (device) member (not shown) and a CPU (computing device) (not shown) of the measurement apparatus 1, thereby electrochemically measuring the amount of an electron carrier to obtain a blood glucose level.

Obtained measurement results are stored in the storage member (memory) (not shown) as data for the biological sample (blood) collected from a fingertip, and displayed on the display (device) member 12.

On the other hand, FIG. 2 is a schematic view of an external appearance of a biological component measurement apparatus 2 in accordance with the present invention, including a cap 28 adapted for collection of a biological sample from a forearm, with the puncture apparatus being integrated thereto. FIG. 2 shows a state where the cap 28 is engaged with the housing 11. In FIG. 2, the difference from the configuration shown in FIGS. 1A and 1B is that a living body contact portion 29 of the cap 28 has a shape adapted for collection of a biological sample from a forearm. The living body contact portion 29 is in such a shape normally of a curved surface with a diameter larger than that for a fingertip as to fit well the skin of the forearm of the subject against which it is pressed. The cap 28 includes a biological sample collection opening 27, corresponding to the opening 17 shown in FIGS. 1A and 1B, providing a mechanism where, through the opening 27, the puncturing member which is attached via the puncturing member attachment opening 67 (see, FIG. 1B) protrudes, thereby puncturing the skin of a subject. The cap 28 can be detachably attached to the housing 11 in the same way as described in FIGS. 1A and 1B. Note that an external view, where the cap 28 is detached from the housing 11, and the description therefor are omitted here because these are substantially the same as those for FIGS. 1A and 1B.

As described above, the caps (18, 28) shown in FIGS. 1A and 1B and FIG. 2 are designed so as to be adapted to the shape of each collection site of the biological sample, and can be detachably attached to the housing 11. Therefore, when changing collection sites for the biological sample, a user has only to exchange the caps (18, 28) so as to be compatible with the change of the collection sites. Thus, it is possible to collect biological samples from a plurality of different sites using a single measurement apparatus. Note that although only examples where sampling is performed at a fingertip or a forearm are explained here, the present invention is not limited to these examples, and it is possible to use a cap (18, 28) which is designed so as to be adapted to an other sampling site (i.e., a palm, an upper arm, a thigh, an abdomen, or the like).

In addition, as is apparent from FIGS. 1A and 2, and the above description, the cap (18, 28) protects the puncture needle at times other than the time of puncturing.

Measurements of blood glucose levels from a sampling site other than a fingertip have recently become more common because of merits, such as, less pain no scar remaining on the fingertip. However, it is pointed out that there may be deviations in the blood glucose level between the fingertip and the forearm when the blood glucose level fluctuates largely, (e.g., after a meal). In such a case, it is recommended, even for those who normally perform measurements at their forearm, to perform measurements at their fingertip.

In such circumstances, the measurement apparatus according to the present invention is useful for the user in that it is not necessary to change the body of the measurement apparatus for each sample collection site and a mere change of the caps makes it possible to take measurements from a plurality of sample collection sites using a single measurement apparatus.

Note that the shape of the biological component measurement apparatus according to the present embodiment as shown in FIGS. 1A and 1B and 2 is simplified merely for the sake of explanation, and no limitation to such a box-like shape is intended. It goes without saying that other shapes that are easy to grip by hand or fingers (e.g., a rod-like shape, a flat shape, a pen-like shape, etc.) are applicable (the same applied to embodiments described below).

SECOND EMBODIMENT

Next, referring to FIGS. 3-7, a second embodiment of the present invention will be described.

Figure 3:
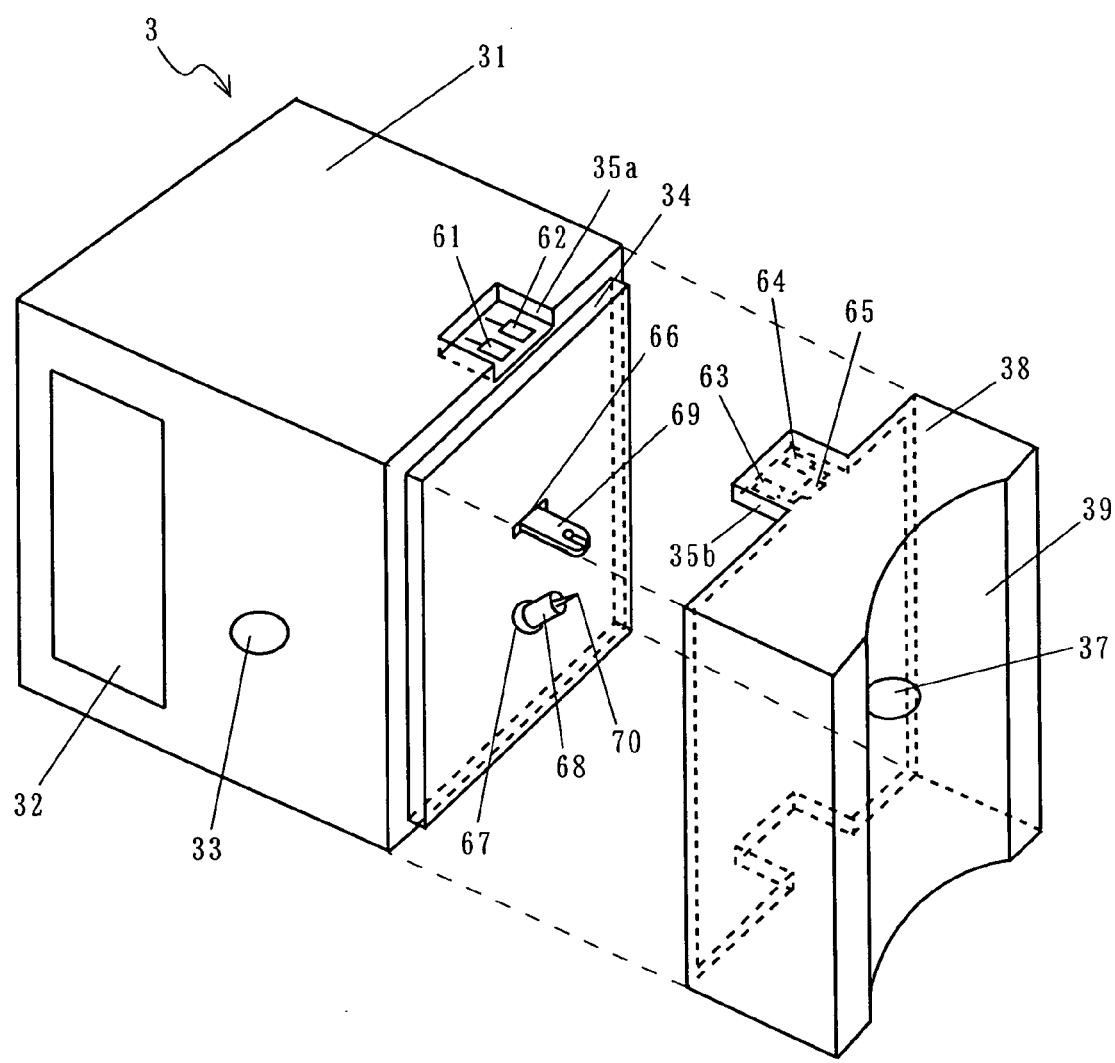
FIG. 3 is a schematic view illustrating an external appearance of a biological component measurement apparatus 3 integrated with a puncture apparatus in accordance with an embodiment of the present invention, including a cap recognition mechanism (which includes electric terminals 61, 62, 63 and 64, and a constant resistance 65).

FIG. 3 is a schematic view illustrating an external appearance of a biological component measurement apparatus 3, including a cap recognition mechanism (which includes terminals 61, 62, 63 and 64, and a constant resistance 65), with a puncture apparatus being integrated into the measurement apparatus. The biological component measurement apparatus 3 of the present invention includes a housing 31 made of a material such as plastic, which houses a body of the measurement apparatus and constitutes a part thereof, and a cap 38 which is detachably attachable to the housing 31. FIG. 3 shows a state where the cap 38, which is designed for a fingertip, is detached from the housing 31.

The biological component measurement apparatus 3 shown in FIG. 3 further includes a cap recognition mechanism in a portion where the housing 31 and the cap 38 are engaged with each other. The measurement apparatus further includes a memory (device) 102 (FIG. 4) for storing data and a timer for measuring time for a measurement operation (not shown), both of which are housed within the housing 31. Other features are basically the same as those shown in FIGS. 1A and 1B, and therefore, the detailed descriptions thereof are omitted hereinafter.

In FIG. 3, the housing 31 has provided thereon a display member 32 for displaying results measured by a biosensor, (e.g., a concentration of a biological component, which is comprised of a liquid crystal digital display or the like, and a switch 33 for starting a measurement. Furthermore, the housing 31 includes a biosensor 69, an opening 66 for attaching the biosensor, a puncture needle holder 68, a puncture needle 70, and an opening 67 for a puncturing member. The housing 31 also includes a gasket 34 for sealing a portion where the cap 38 is engaged with the housing (or another sealing mechanism may be included).

The cap 38 is detachably attached to the housing 31 by means of friction engagement, detent or the like. The cap 38 includes a living body contact portion 39 designed so as to have a curvature configuration that fits a fingertip well, and a biological sample collection opening 37. Note that because the cap 38 is detachable, any cap whose living body contact portion 39 is designed for a site other than a fingertip (e.g., a forearm, a thigh, or the like), similar to the living body contact portion 29 shown in FIG. 2, for example, can be used depending on the sampling sites.

In the second embodiment of the present invention, the housing 31 further includes a recess 35a which is engaged with a protrusion 35b of the cap 38 at the time of attachment of the cap 38. The terminals (second pair of electric contacts) 61 and 62 made of a conductive material such as copper are provided in the recess 35a of the housing 31, and when the cap 38 is engaged with the housing 31, terminals 61 and 62 are brought into contact with the terminals (pair of electric contacts) 63 and 64, which are also electrically conductive and provided on a surface of the protrusion 35b that is in contact with the recess 35a of the housing.

The constant resistance 65 specific to the cap 38 is provided on the protrusion 35b between the terminals 63 and 64, so as to be electrically connected.

On the other hand, the terminals 61 and 62 in the recess 35a of the housing 31 are connected to a resistance measurement device (not shown) housed in the housing 31. When a circuit is formed by attaching the cap 38 to the housing 31 so that terminals 61 and 62 in the recess 35a are brought into contact with the terminals 63 and 64 on the protrusion 35b, the resistance measurement device detects a resistance value of the constant resistance 65 and transmits it to the CPU 101 (FIG. 4) of the measurement apparatus 3, which is also housed in the housing 31. The CPU 101 is able to recognize the biological sample collection site (e.g., a fingertip) by referring to data (not shown) previously stored in the memory 102 of the housing 31, which contains specific sample collection sites assigned to resistance values of the constant resistance.

In this way, information about sample collection sites is stored in the memory 102 housed within the housing 31, together with the measurement values, and displayed, as necessary, on the display member 32, together with the measurements values. Furthermore, as necessary, information about measurement times measured by a timer (not shown) housed within the housing 31 is stored in the memory, together with the measurement values.

Thus, according to the present invention, biological samples from a plurality of different sites can be collected using a single measurement apparatus. In addition, the information about sample collection sites can be stored in and/or displayed on the measurement apparatus, together with measured values of biological components in the samples. As such, a user can simultaneously recognize the measurement values and the sample collection sites using the biological component measurement apparatus of the present invention. Further, because the user can correct the measurement values based on information about sample collection sites and sampling times, as necessary, it is possible to know blood glucose values of the subject more accurately. As a result, control of the subjects' blood glucose can be made more securely.

Since the present embodiment includes the memory 102, blood glucose values recorded in a chronological order are stored together with information about locations of sampling sites. Therefore, fluctuation of blood glucose values of the subject can be monitored more accurately, whereby it is possible to carry out more reliably a treatment aimed at improving the blood glucose level.

Figure 4:
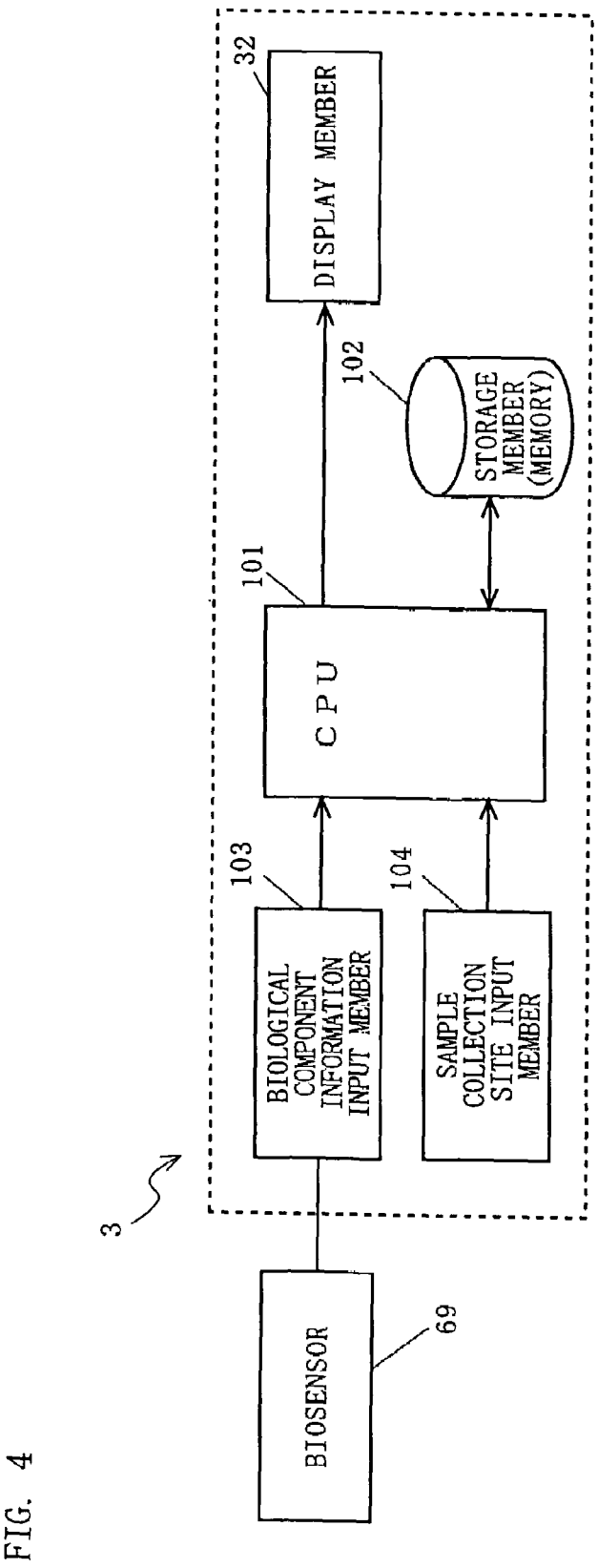
FIG. 4 is a block diagram illustrating an entire configuration of a biological component measurement apparatus 3 in accordance with an embodiment of the present invention (note that a cap 38 and a puncturing member are omitted).

FIG. 4 is a block diagram illustrating an entire configuration of the biological component measurement apparatus 3 in accordance with the second embodiment of the present invention (note that the cap 38 and the puncturing member are omitted). The biological component measurement apparatus 3 includes the CPU 101, the memory 102, a biological component information input member 103 for entering biological component information from the biosensor 69, a sample collection site input (device) member 104 for entering biological component collection sites, and a display member 32. The biological component measurement apparatus 3 further includes a timer (not shown) for entering time.

The biological component information input member 103 is composed of, for example, a slot (not shown) for attaching the biosensor 69, an electric contact (not shown) provided in the slot for engagement with a terminal of the biosensor 69, and an electric circuit (not shown), which is electrically connected to the electric contact, for converting current values from the biosensor 69 into voltage pulses before entering them into the CPU 101. The biological component information input member is operable to enter information about substrate concentrations from the biosensor 69 into the CPU 101. For example, the biological component information input member 103 may include a power supply for applying voltage to a measurement electrode of the biosensor under the control of the CPU 101, a current/voltage converter circuit (not shown) for producing voltage by converting current produced by contact between the measurement electrode of the biosensor and a sample, and an A/D converter circuit (not shown) for converting a voltage value from the current/voltage converter circuit into a pulse.

On the other hand, the sample collection site input member 104 is composed of, for example, the recess 35a provided to the housing 31, the terminals 61 and 62 provided in the recess 35a FIG. 3), and a resistance measurement device (not shown), which is electrically connected to the terminals 61 and 64 and to the CPU 101. The sample collection site input member 104 is operable to detect a resistance value specific to the cap 38 (FIG. 3) and transmits it to the CPU 101.

The memory 102 is comprised of a storage medium such as a RAM, a ROM, an external memory device, or the like, and stores information from the biological component information input member 103, the sample collection site input member 104, the CPU 101, and so on.

The display member 32 is composed of a display device such as a liquid crystal digital display or the like, and displays information about measurement results, measurement times, measurement sites, and so on.

Figure 5:
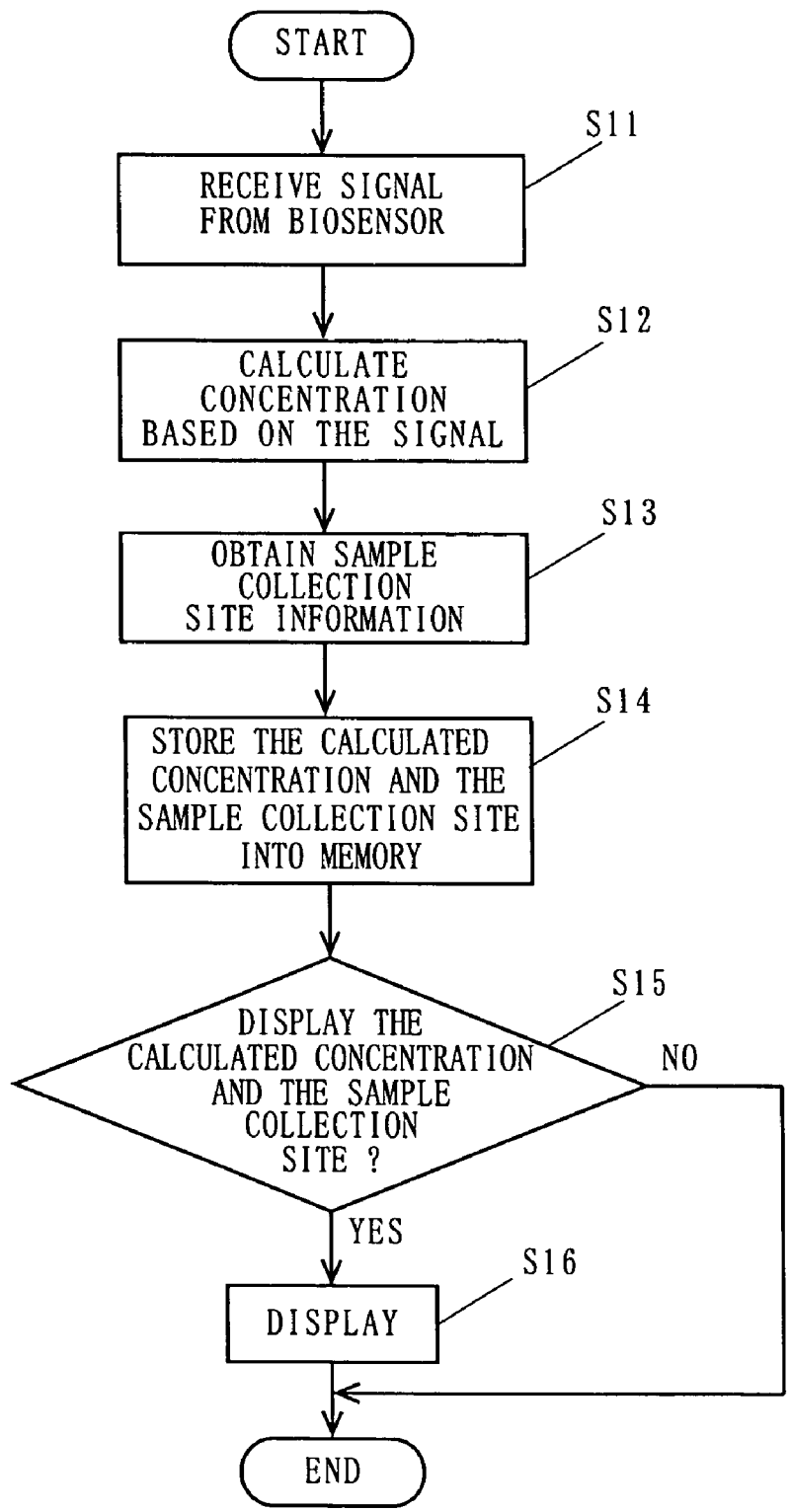
FIG. 5 is a flow chart illustrating a process operation of a CPU 101 of the measurement apparatus whose entire configuration is illustrated in FIG. 4.

FIG. 5 is a flow diagram illustrating a process operation of the CPU 101 of the measurement apparatus whose entire configuration is illustrated in FIG. 4.

The process operation shown in FIG. 5 is started by the user's action of pressing or touching the switch 33. When the user operates the switch 33, the CPU 101 activates the puncture mechanism of the measurement apparatus 3 so as to puncture the subject's skin at a measurement site to cause blood to exit therefrom. At step S11, the CPU 101 obtains an electric signal, which contains information about the concentration of a biological component (a substrate), from the biosensor 69 via the biological component information input member 103. Specifically, the biosensor 69 is brought into contact with the blood sample due to puncturing, and the blood sample is collected into a sample chamber of the biosensor 69. After a sufficient amount of blood is collected, voltage is applied between measurement electrodes of the biosensor 69 and the electric signal, which contains information about the substrate concentration, is obtained from the biosensor 69. Then, at step S12, the CPU 101 calculates the substrate concentration based on the signal. For calculation of the substrate concentration, an algorithm previously stored in the memory 102 is applied for correlation with the substrate concentration in the sample. At step S13, the CPU 101 obtains a specific sample collection site based on collection site information (e.g., a resistance value of the constant resistance 65) entered via the sample collection site input member 104. At step S14, the calculated concentration and the specified sampling site are stored into the memory 102.

At step S15, whether to display the information is determined. If it is determined to be displayed (S15: Yes), results are displayed on the display member 32 at step S16 before ending the process. If it is determined not to be displayed (S15: No), the process is terminated. Here, the determination as to whether to display the information may depend on, for example, the user's operation. For example, a display button (not shown) may be provided to the measurement apparatus 3, such that the user can select display/non-display by pressing the button. Note that instead of providing such a step (i.e., step S15) of determining display/non-display, all measurement results may be displayed.

In this way, the measurement results can be correlated with the collection sites of the sample (i.e., blood). By recording the measurement results and the collection sites of the blood in association with each other in the memory, it is rendered possible to utilize measurement data more effectively for managing blood glucose levels of a subject. When the calculated concentration and the sampling sites are stored to the memory 102 at step S14, sampling times may also be stored as necessary, making it possible to analyze measurement values in a chronological manner.

In the present embodiment, although the puncture member and the biosensor are separately contained in the measurement apparatus, the puncture member and the biosensor may be integrally formed.

In addition, in the second embodiment, although the cap 38 which is configured to fit a surface of a blood collection site, and the cap recognition mechanism (61, 62, 63, 64 and 65) of the housing 31 are used to recognize the blood collection site, a sample collection site recognition method is not limited to this.

Figure 6:
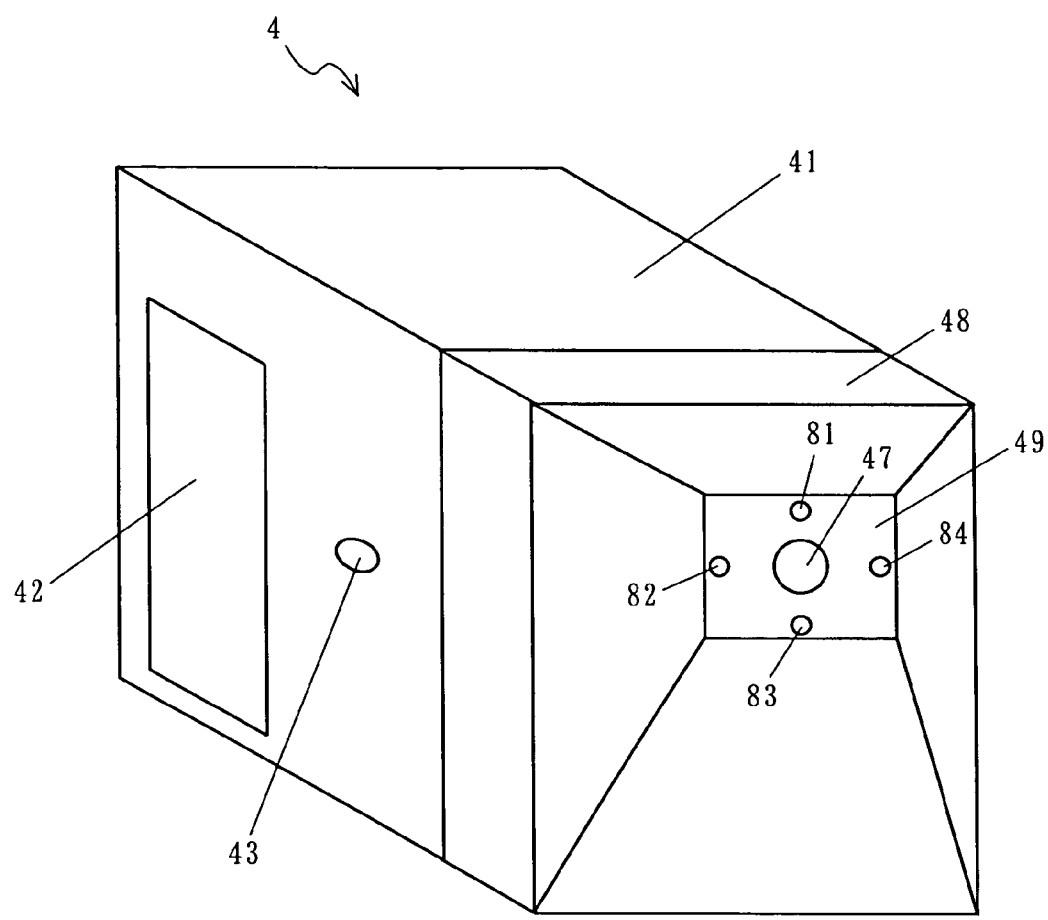
FIG. 6 is a schematic view illustrating an external appearance of a biological component measurement apparatus 4 in accordance with an embodiment of the present invention, including a cap that includes a living body contact portion having provided thereon a plurality of sensors that sense a state of contact with skin.

For example, as shown in FIG. 6, a plurality of sensors for detecting a state of contact with skin (81, 82, 83 and 84) may be provided around a biological sample collection opening 47 provided in a living body contact portion 49 of a cap 48, such that the blood collection site can be recognized based on a combination of signals detected by the sensors.

More specifically, the cap 48 includes, at the top, the living body contact portion 49 having a generally flat surface. As shown in FIG. 6, it is preferred that the living body contact portion 49 has a relatively small plane on the top of the cap 48 so as to fit both a site having a relatively small contact surface such as a fingertip and a site having a relatively large contact surface such as a forearm. The sensors 81, 82, 83 and 84 for detecting contact with skin are provided on the living body contact portion 49. In the case of collecting a blood sample from a fingertip, for example, only a part of the four sensors (e.g., sensors 81 and 83) detects contact with skin because an area of the skin, which is in contact with the living body contact portion 49, is small. On the other hand, in the case of collecting a blood sample from a forearm, all of the four sensors (e.g., sensors 81, 82, 83 and 84) detect contact with skin because an area of the skin, which is in contact with the living body contact portion 49, is relatively large.

The sensors (81, 82, 83 and 84) are connected to a CPU (not shown) in the housing 41 of the measurement apparatus. The CPU is set so as to determine that the sampling site is a forearm, if a skin contact detection signal is received from all of the four sensors, and determine that the sampling site is a fingertip, if the skin contact detection signal is received from a part of four sensors (e.g., two sensors (being sensors 81 and 83), by making it possible to enter information about sampling. Examples of such sensors for detecting a state of contact with skin include, but are not limited to, a touch sensor, a tactile sensor, a method for measuring a change in resistance using electrodes, and a method for measuring reflected light using a light source. The sensors 81, 82, 83 and 84 may be connected with the CPU housed in the housing 41 by means of electric contacts provided where the housing 41 and the cap 48 are engaged with each other in the same way as shown in FIG. 3. In addition, the sensors may be provided not on the cap 48 but on the housing 41. In such a case, the cap 48 may include (an) opening(s) for those sensors (not shown).

Note that the number of the sensors to be provided may normally be more than or equal to two and is not limited to four as in the above example.

Alternatively, in still another method for sample collection site recognition, a plurality of input switches, for example, may be used as sample site collection input means. Specifically, a switch for selecting a forearm and a switch for selecting a fingertip (not shown), for example, which are connected to a CPU within the housing, may be provided on the housing of the apparatus body. By pressing either of the switches to start a measurement procedure depending on sampling sites, the measurement procedure is started, making it possible to enter sample collection sites. Such switches may be push buttons or the like. Note that the switches for entering sample collection sites may be provided together with switches for starting measurements, or may also be used as the switches for starting measurements.

THIRD EMBODIMENT

A third embodiment of the present invention is described referring to FIGS. 7-10.

As described above, fluctuations in blood glucose levels are large immediately after the subject takes a meal, depending on sampling sites. In such a case, fluctuation behavior of blood glucose levels measured at a forearm is often delayed for some time as compared to fluctuation behavior of blood glucose levels measured at a fingertip (see John M. ELLISON, Diabetes Care vol. 25, No. 6, 961-964, (2002)). Accordingly, it is conceivable that by previously creating a correction equation based on measurement results obtained under the above conditions, the blood glucose levels measured at a forearm can be corrected depending on an elapsed time after a meal.

Here, measurement values obtained at a fingertip and a forearm before and after a meal as described in the aforesaid John M. ELLISON (2002) are taken as examples of the measurement values obtained under the above conditions. John M. ELLISON (2002) describes that there is substantially no difference between measurement values obtained at a fingertip and at a forearm when the stomach is empty, while measurement values obtained at the fingertip at 60 minutes, 90 minutes, and 120 minutes after a meal are higher by about 10%, about 8%, and about 2%, respectively, than measurement values obtained at the forearm at the same time intervals after the meal. At 150 minutes after the meal, there is substantially no difference between measurement values obtained at the fingertip and at the forearm, while at 180 minutes after the meal, measurement value obtained at the fingertip is lower by about 5% than measurement value obtained at the forearm. Therefore, in the case where a measurement is performed for blood collected from the forearm at, for example, 60 minutes after the meal, by raising a value of an obtained result by about 10%, it is possible to estimate it as a value obtained from the fingertip, Further, at 180 minutes after the meal, by lowering a value of a measurement result obtained from blood collected from the forearm by about 5%, it is possible to estimate it as a value obtained from the fingertip. Note that this data merely presented as an example, and other degrees of correction may be applicable depending on subjects.

Figure 7:
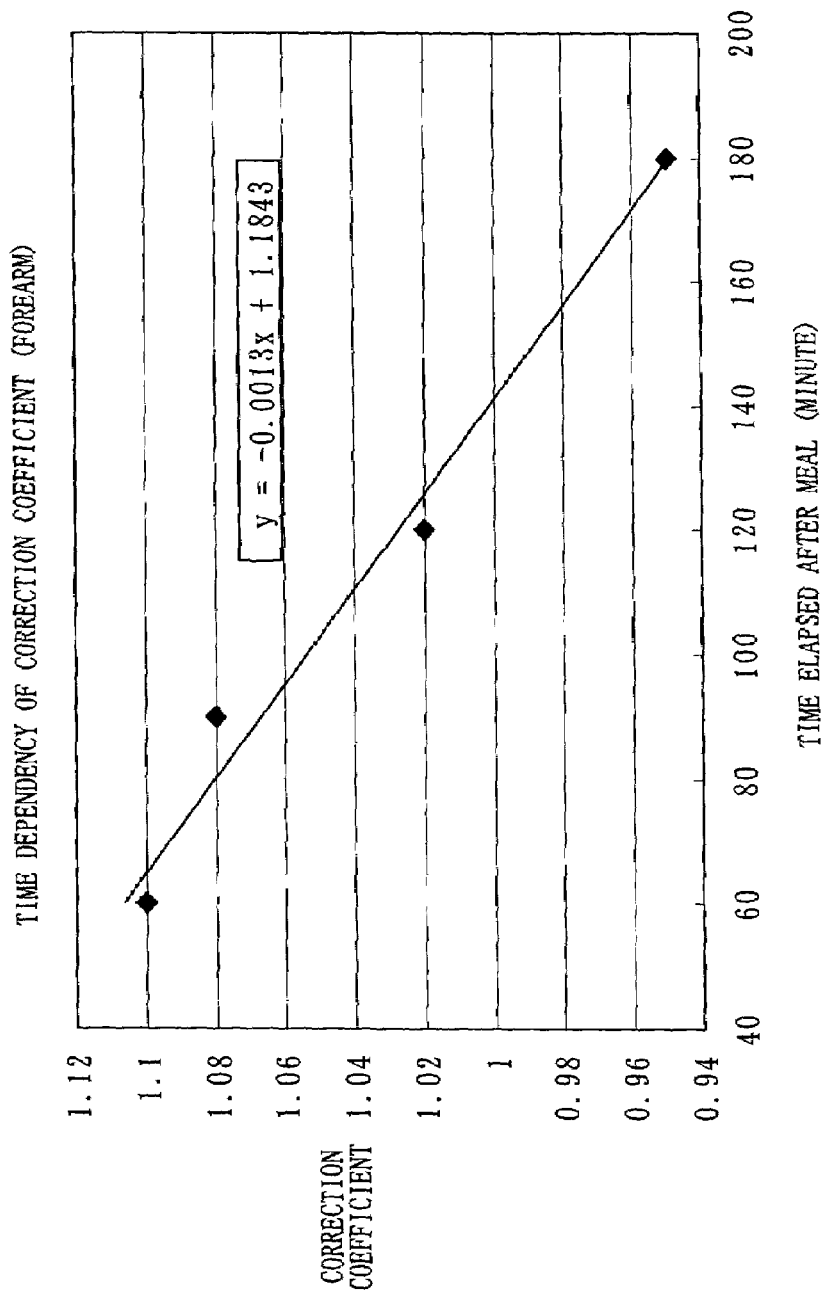
FIG. 7 is a graph showing time dependency of a correction coefficient for correcting measurement values based on an elapsed time after a meal.

Such correction can be made by multiplying an actual measurement value by a correction coefficient as shown in FIG. 7. FIG. 7 shows time dependency of the correction coefficient obtained based on data from the aforesaid John M. ELLISON (2002). In the same figure, the vertical axis (y-axis) indicates the correction coefficient for making correction for blood samples collected at a forearm, and the horizontal axis (x-axis) indicates an elapsed time after a meal. Note that although the correction coefficient is assumed to be expressed by a linear function of the elapsed time after a meal, it is not intended to be limited thereto, and it may be expressed by other functions (e.g., a quadratic function, an exponential function, etc.). Corrected values can be obtained by multiplying values of glucose concentration in blood measured at a forearm at time intervals after a meal by the correction coefficient shown in the graph of FIG. 7. For example, in the case where a value of glucose measured at a forearm at 60 minutes after a meal is 70 mg/dl, if the correction coefficient shown in FIG. 7 is used, the measured value is multiplied by a correction coefficient for a 60-minute time point (i.e., 1.11), resulting in a corrected value of 77.4 mg/dl.

Alternatively, a correction factor may be determined by referring to a correction table, which is previously created based on experimental results for blood sample collection sites and elapsed times after a meal. Preferably, the experimental data is obtained for each subject.

As such, results obtained based on blood collection at a site other than a fingertip (e.g., a forearm) are corrected in accordance with an elapsed time after a meal, so that they can be compared with blood glucose levels measured for blood collected from a fingertip by correcting the results for an elapsed time after a meal, thereby making it possible to monitor accurate blood glucose levels without relying on measurement time or measurement sites. Hereinafter, an embodiment, where such an operation is performed with a measurement apparatus, will be described with reference to the drawings.

Figure 8:
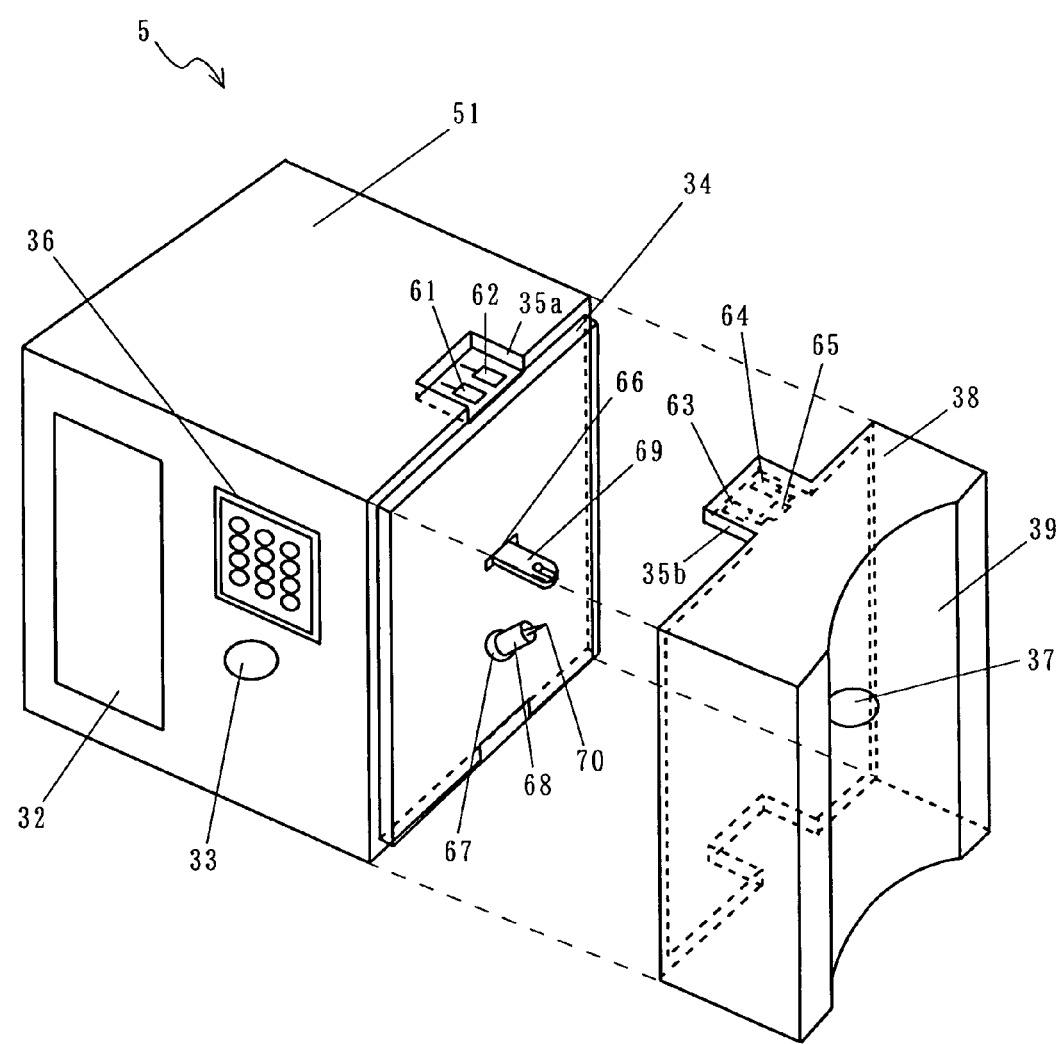
FIG. 8 is a schematic view illustrating an external appearance of a biological component measurement apparatus 5 in accordance with an embodiment of the present invention, which is capable of entering an elapsed time after a meal.

FIG. 8 is a schematic view illustrating a configuration of a biological component measurement apparatus 5 in accordance with the third embodiment of the present invention, which is capable of entering an elapsed time after a meal. In the same figure, the measurement apparatus 5 includes a housing 51 and a cap 38. The difference between the measurement apparatus shown in FIG. 8 and the measurement apparatus shown in FIG. 3 is that the measurement apparatus 5 shown in FIG. 8 includes a mealtime input member 36 which is a means for entering an elapsed time after a meal. Because other features are the same as those in FIG. 3, descriptions thereof will be omitted.

The mealtime input member 36 includes a push button unit by which the user can enter, for example, numbers 0-9 for inputting a mealtime or an elapsed time after the meal. It is not limited to the above push button unit, and other input means, including a touch panel, can be used as long as the mealtime or an elapsed time after a meal can be entered.

Figure 9:
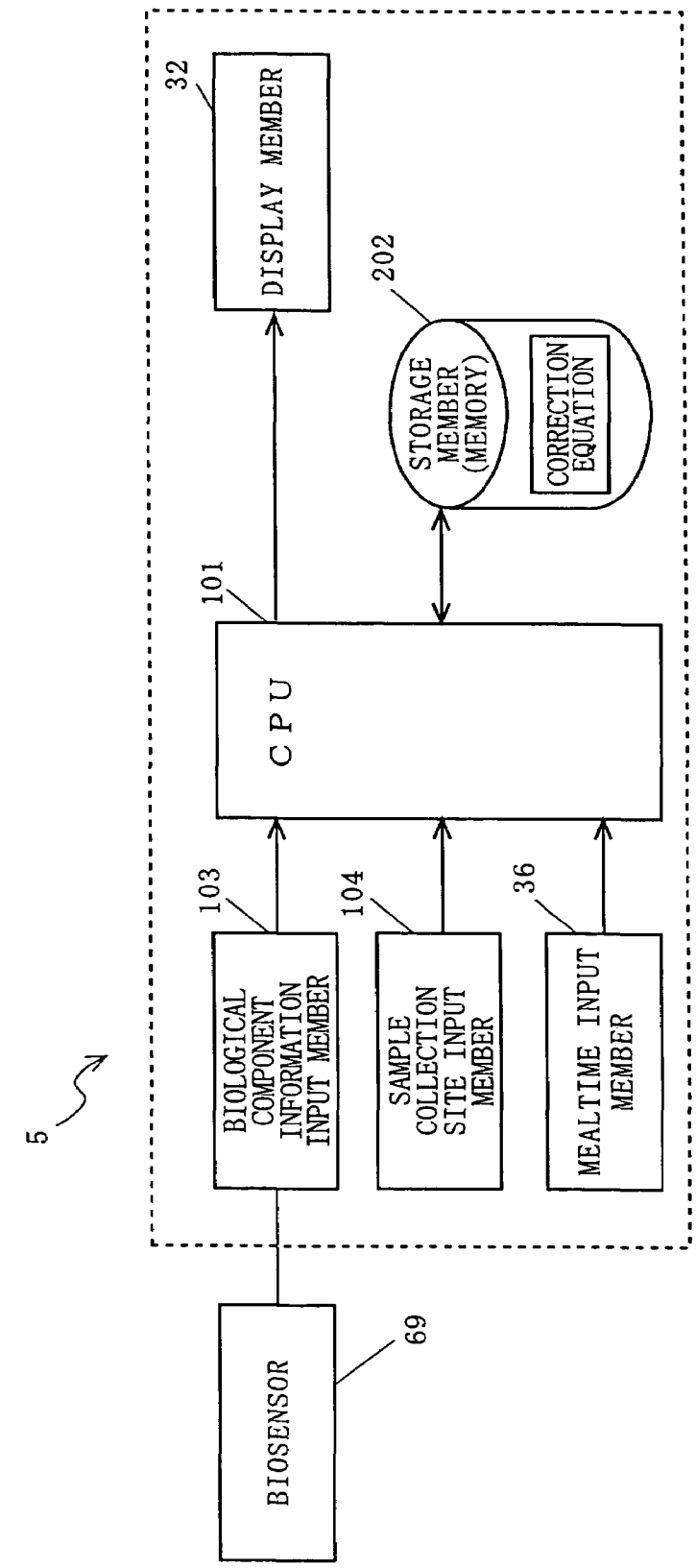
FIG. 9 is a block diagram illustrating an entire configuration of the biological component measurement apparatus in accordance with the embodiment of the present invention shown in FIG. 8.

Referring to FIG. 9, the third embodiment of the present invention is further described. FIG. 9 is a block diagram illustrating an entire configuration of the biological component measurement apparatus in accordance with the third embodiment of the present invention, whose external appearance is schematically shown in FIG. 8 (note that the cap 38 and the puncture member are omitted). This diagram is different from the block diagram shown in FIG. 4 in that the mealtime input member 36 is further included, and a storage member 202 has stored therein a correction equation or a correction table for correcting measured values based on an elapsed time after a meal and sampling sites.

Once the user enters a mealtime via the mealtime input member 36, information thereabout is transmitted to the CPU 101 and, as necessary, stored into the memory 202. This information about the mealtime is utilized for correcting substrate concentration in a sample, which is measured by a biosensor, in accordance with the elapsed time after a meal. Note that the elapsed time after a meal may be directly entered instead of the mealtime.

The memory 202 is composed of a storage medium, such as a ROM, a RAM, an external memory device or the like, and stores information from the biological component information input member 103, the sample collection site input member 104, the mealtime input member 36, the CPU 101, etc. In addition, the memory 202 has previously stored there in a correction equation or a correction table for correcting measurement values in accordance with the elapsed time after a meal or sampling sites.

Figure 10:
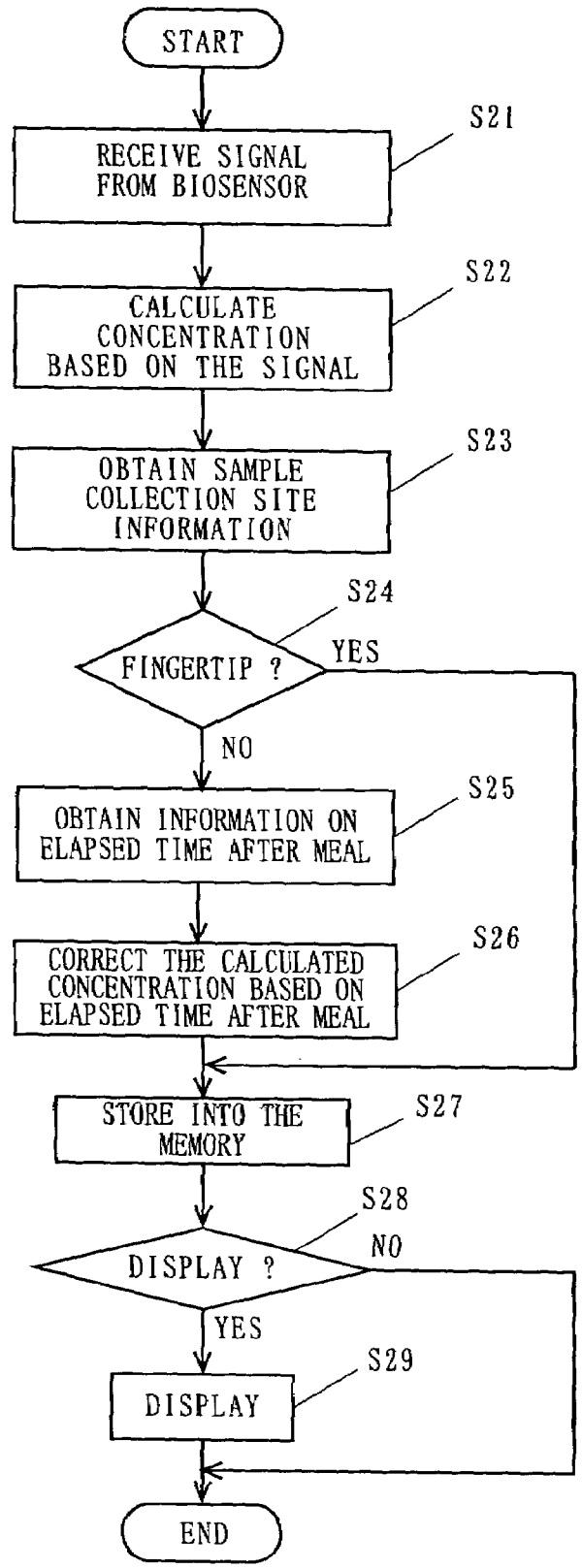
FIG. 10 is a flow chart illustrating a processing operation of a CPU 101 of the measurement apparatus whose entire configuration is illustrated in FIG. 9.
Figure 11:
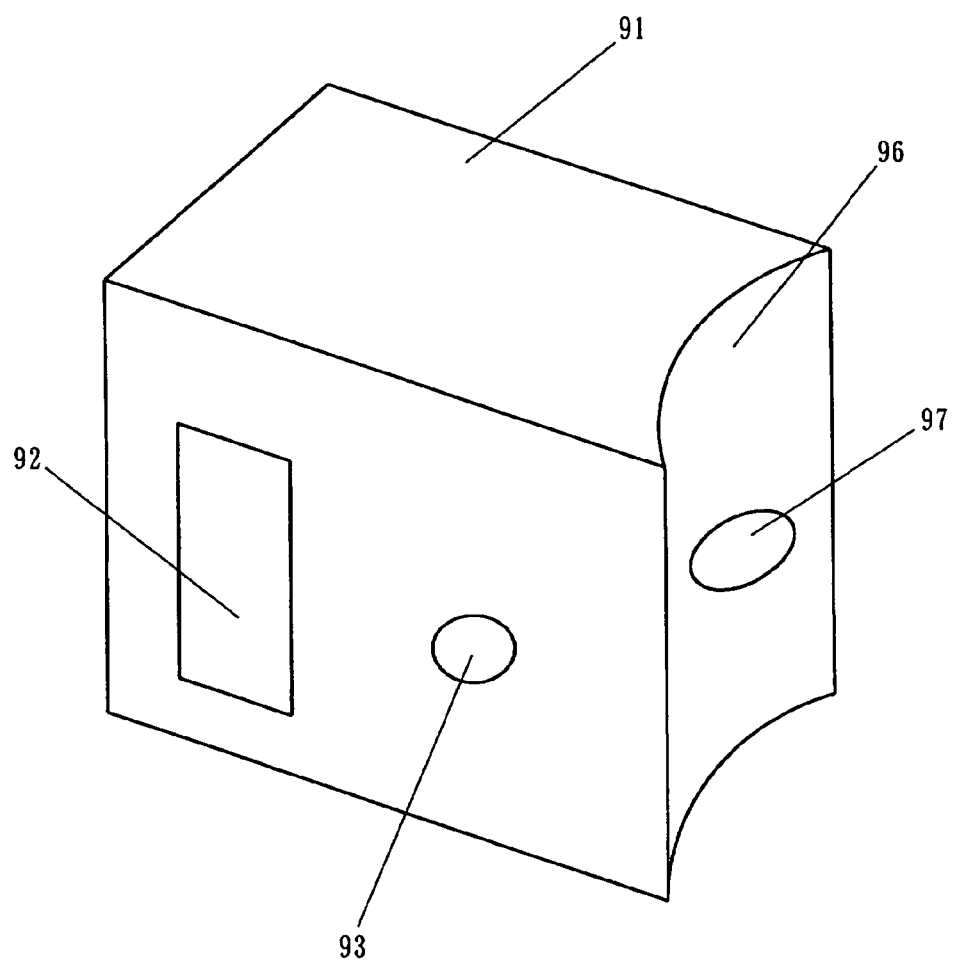
FIG. 11 is a schematic diagram of a conventional biosensor for measuring glucose.

FIG. 10 is a flow chart illustrating a process operation of the CPU 101 of the measurement apparatus whose entire configuration is illustrated in FIG. 9.

The process operation shown in FIG. 10 is started with the user's action of, for example, pressing or touching the switch 33. Once the user operates the switch 33, the CPU 101 activates the puncture mechanism of the measurement apparatus 5 to puncture the subject's skin at a measurement site so that blood exits out. At step S21, the CPU 101 obtains an electrical signal, which contains information on the concentration of a biological component (glucose, here), from the biosensor 69 via the biological component information input member 103. Specifically, the biosensor 69 is brought into contact with the blood due to puncturing, and the blood sample is collected to a sample chamber of the biosensor 69. After a sufficient amount of blood is collected, voltage is applied between measurement electrodes of the biosensor 69, and the electric signal, which contains information on the substrate concentration, is obtained from the biosensor 69. Then, the CPU 101 calculates the substrate concentration based on the signal. For the calculation of the substrate concentration, an algorithm previously stored in the memory 202 is applied for correlation with the substrate concentration in the sample to the signal. At step S23, the CPU 101 obtains sampling site information (e.g., a resistance value of the constant resistance 65) entered via the sample collection site input member 104, thereby recognizing a specific collection site.

At step S24, it is determined whether the collection site is a fingertip. If it is a fingertip (S24: Yes), then at step S27, the calculated concentration and the specified collection site are stored into the memory 202. Then, at step S28, it is determined whether to display the information. If it is determined to be displayed (S28: Yes), then, at step S29, results are displayed on the display member 32 before ending the process. If it is determined not to be displayed (S28: No), the process is terminated. Here, the determination as to whether to display the information may depend on, for example, the user's operation. For example, a display button or the like (not shown) may be provided to the measurement apparatus 5 such that the user can select display/non-display by pressing the button. Note that instead of providing such a step (step S28) of determining display/non-display, all measurement results may be displayed.

On the other hand, at step S24, if the sample collection site is not a fingertip (e.g., a forearm) (S24: No), at step 25, the elapsed time after a meal is obtained. At step S26, a correction coefficient or a correction factor is obtained by referring to the correction equation (such as that shown in FIG. 7) or the correction table stored in the memory 202, and the correction coefficient and the correction factor are used to obtain measurement values corrected based on the elapsed time after a meal. Note that it is often the case that the correction coefficient or the correction factor is different among subjects, and therefore it is preferable that they are obtained for each subject. Then at step S27, the corrected measurement values are stored into the memory 202, together with the collection site information. Then, at step S28, it is determined whether to display the information. If it is determined to display the information (S28: Yes), then, at step S29, results are displayed on the display member 32 before ending the process. If it is not determined to display the information (S28: No), then, the process is terminated.

Thus, in the third embodiment, when a measurement value of substrate concentration in a sample considerably varies with time after a meal as compared with a case of collecting a sample from a fingertip, as in the case of measuring blood glucose values for blood sampled from a site other than a fingertip, (e.g., a forearm) the substrate concentration in a sample collected at a site other than a fingertip is corrected using the above-mentioned correction coefficient, so that it can be compared with other measurement results obtained for samples sampled from a fingertip.

Thus, it is possible to accurately monitor the substrate concentration (e.g., blood glucose levels) irrespective of sampling sites, whereby it is possible to perform an appropriate treatment on the subject.

Note that although the above example has been described with respect to a case where measurement values obtained from sites other than a fingertip are corrected based on the measurement values obtained from a fingertip, a site from which a measurement value to be referenced to is obtained can be optimally selected depending on the purpose.

Also, the above example has been described with respect to a method for inputting collection site information, which uses, but not limited to, a sampling site recognition mechanism provided in a portion where a cap is engaged with an apparatus body. However, in other embodiments, sensors as shown in FIG. 6 may be used, or (an) additional switch(s) for entering sampling sites may be used.

While the invention has been described in detail, the foregoing description is in all aspects illustrative and not restrictive. It is understood that numerous other modifications and variations can be devised without departing from the scope of the invention.

Plastic or the like is preferable for a material of the cap in the first to third embodiments. If an elastic material such as rubber is used to form a portion which is caused to be in contact with a living body, adhesion with skin is enhanced, resulting in reliable measurements.

The biosensors described in the first to third embodiments, may be any sensors that can identify or quantify a specific component in a biological sample. The measurement method used thereby may be electrochemical or optical.

For example, the biosensors described in the first to third embodiments may use, as an enzyme, glucose oxidase or glucose dehydrogenase, which specifically reacts with glucose, and also use potassium ferrocyanide as an electron carrier, and it may use electrodes to obtain an electrochemical signal response, thereby quantifying glucose. They are not limited to the enzyme and the electro carrier as mentioned above.

Oxidoreductase, which corresponds to a substrate targeted for measurement, contained in a biological sample and targeted for measurement are used, and examples thereof include fructose dehydrogenase, alcohol oxidase, lactate oxidase, cholesterol oxidase, cholesterol dehydrogenase, xanthine oxidase, amino acid oxidase, and the like.

Examples of the electron carrier include p-benzoquinone, phenazine methosulfate, methylene blue, ferrocene derivative and the like. Also, a current response can be obtained when oxygen is used as the electron carrier. One or two or more electron carriers as mentioned above are used.

Also, in the above first to third embodiments, a biological sample collection site is a fingertip or a forearm, but it is not limited to them. For example, the sampling site may be a palm, an upper arm, a thigh, an abdomen, or the like. A palm can be a ball of thumb, or a hypothenar area.

In the case where measurements are performed using a cap, the shape of the cap can be determined depending on shapes of sampling sites.

Also, a biological sample used in the above-described embodiments is, but not limited to, whole blood. Any sample can be used as long as it contains a test substance whose measured value varies depending on collection sites and collection time. In addition, the substrate (measurement object) is not limited to glucose. Other substrates contained in other biological samples, such as, interstitial fluid, saliva, sweat, urine, bone marrow liquid, etc., can also be used.

The biological component measurement apparatus of the present invention correlates measurement results with collection sites of biological samples, making it possible to more accurately interpret measured values, and therefore, is useful as, for example, a biosensor measurement apparatus for accurately monitoring the condition of a subject.

The invention claimed is:

1. A biological component measurement apparatus set comprising:
   a biosensor measurement device having a body;
   a plurality of caps for detachable engagement with said body of said biosensor measurement device, said plurality of caps including caps corresponding to different sample collection sites, each of said caps having a skin contact surface with an opening therein; and
   a puncture mechanism having a puncture needle and being operable to puncture skin of a subject for collecting a sample of blood from a sample collection site, wherein:
      said skin contact surface of said caps are shaped to fit a surface shape of the skin to be punctured by said puncture mechanism;
      when a cap of said plurality of caps is detachably engaged with said body of said biosensor measurement device and said skin contact surface of said cap is brought into contact with the skin to be punctured, said puncture needle is operable to move through said opening of said skin contact surface and puncture the skin to produce the sample of blood; and
      said biosensor measurement device further comprises:
         a biological component information input device having a biosensor attachment member and a biosensor for attachment therewith operable to receive the sample of blood and produce measurement information, said biological component information input device being operable to receive the measurement information produced by said biosensor;
         a sample collection site input device operable to receive information regarding the sample collection site;

a memory device;
a computing device operable to calculate a substrate concentration of the sample of blood according to the measurement information received by said biological component information input device; and
a display device operable to display the substrate concentration calculated by said computing device and the information regarding the sample collection site, wherein said memory stores the information regarding the sample collection site and the substrate concentration calculated by said computing device.

2. The biological component measurement apparatus set according to claim 1, wherein said biosensor is a glucose sensor.

3. The biological component measurement apparatus set according to claim 1, wherein:
said caps include a pair of electric contacts on at least a portion thereof for detachable engagement with said body of said biosensor measurement device, said pair of electric contacts including a constant resistance, specific to each cap of said plurality of caps, being connected therebetween;
said sample collection site input device further comprises:
a resistance measurement device on a portion of said body for detachable engagement with said caps and operable to detect the constant resistance when said cap is detachably engaged with said body of said biosensor measurement device, and
a second pair of electric contacts electrically connected to said resistance measurement device and operable to be brought into contact with said pair of electric contacts to form an electric circuit when said cap is detachably engaged with said body of said biosensor measurement device so as to allow said resistance measurement device to detect the constant resistance specific to said cap; and
the sample collection site is determined according to the constant resistance, specific to each cap of said plurality of caps, detected by said resistance measurement device.

4. The biological component measurement apparatus set according to claim 1, wherein:
said biosensor measurement device includes a mealtime input device operable to receive a mealtime or an elapsed time after a meal;
said memory includes a previously stored collection table or a correction equation for correcting the substrate concentration according to the mealtime or the elapsed time after the meal and the sample collection site; and
said computing is operable to access said previously stored correction table or correction equation, and calculate a corrected substrate concentration according to the mealtime or the elapsed time after the meal and the sample collection.

5. The biological component measurement apparatus set according to claim 1, wherein said plurality of caps includes a cap operable to collect the sample of blood form a fingertip and a cap operable to collect a sample of blood from a forearm.

6. The biological component measurement apparatus set according to claim 5, wherein said plurality of caps includes a cap operable to collect the sample of blood from any site selected from the group consisting of a palm, an upper arm, a thigh, and an abdomen.

7. A biological component measurement apparatus set comprising:
a biosensor measurement device having a body;
a plurality of caps for detachable engagement with said body of said biosensor measurement device, said plurality of caps including caps corresponding to different sample collection sites, each of said caps having a skin contact surface with an opening therein; and
a puncture mechanism having a puncture needle and being operable to puncture skin of a subject for collecting a sample of blood from a sample collecting site, wherein:
said skin contact surfaces of said caps are shaped to fit a surface shape of the skin to be punctured by said puncture mechanism;
when a cap of said plurality of caps is detachably engaged with said body of said biosensor measurement device and said skin contact surface of said cap is brought into contact with the skin to be punctured, said puncture needle is operable to move through said opening of said skin contact surface and puncture the skin to produce the sample of blood;
said biosensor measurement device further comprises:
a biological component information input device having a biosensor attachment member and a biosensor for attached therewith operable to receive the sample of blood and produce measurement information, said biological component information input device being operable to receive the measurement information produced by said biosensor;
a sample collection site input device operable to receive information regarding the sample collection site;
a memory device;
a computing device operable to calculate a substrate concentration of the sample of blood according to the measurement information received by said biological component information input device; and
a display device operable to display the substrate concentration calculated by said computing device, wherein said memory stores the information regarding the sample collection site and the substrate concentration calculated by said computing device;
said caps includes a pair of electric contacts on at least a portion thereof for detachable engagement with said body of said biosensor measurement device, said pair of electric contacts including a constant resistance, specific to each cap of said plurality of caps, being connected therebetween;
said sample collection site input device further comprises:
a resistance measurement device on a portion of said body for detachable engagement with said caps and operable to detect the constant resistance when said cap is detachably engaged with said body of said biosensor measurement device; and
a second pair of electric contacts electrically connected to said resistance measurement device and operable to be brought into contact with said pair of electric contacts to form an electric circuit when said cap is detachably engaged with said body of said body of said biosensor measurement device so as to allow said resistance measurement device to detect the constant resistance specific to said cap; and the sample collection site is determined according to the constant resistance, specific to each cap of said plurality of caps, detected by said resistance measurement device.

8. The biological component measurement apparatus set according to claim 7, wherein said biosensor is a glucose sensor.

9. The biological component measurement apparatus set according to claim 7, wherein:

said biosensor measurement device includes a mealtime input device operable to receive a mealtime or an elapsed time after a meal;

said memory includes a previously stored correction table or a correction equation for correcting the substrate concentration according to the mealtime or the elapsed time after the meal and the sample collection site; and said computing device is operable to access said previously stored correction table or correction equation, and calculate a corrected substrate concentration according to the mealtime or the elapsed time after the meal and the sample collection.

10. The biological component measurement apparatus set according to claim 7, wherein said plurality of caps includes a cap operable to collect the sample of blood from a fingertip and a cap operable to collect a sample of blood from a forearm.

11. The biological component measurement apparatus set according to claim 10, wherein said plurality of caps includes a cap operable to collect the sample of blood from any site selected from the group consisting of a palm, an upper arm, a thigh, and an abdomen.

12. A biological component measurement apparatus comprising:

a body; and a puncture mechanism operable to puncture skin of a subject for collecting a sample of blood form a sample collection site, said puncture mechanism comprising:

a puncture needle; and a cap, including a skin contact surface having an opening therein, detachably engaged with said body of said biological component measurement apparatus, wherein:

when said skin contact surface of said cap is brought into contact with the skin to be punctured, said puncture needle is operable to move through said opening of said skin contact surface and puncture the skin to produce the sample of blood;

said biological component measurement apparatus further comprises:

a biological component information input device having a biosensor attachment member and a biosensor attached therewith operable to receive the sample of blood and produce measurement information, said biological component input device being operable to receive the measurement information produced by said biosensor;

a sample collection site input device operable to receive information regarding the sample collection site;

a memory device;

a computing device operable to calculate a substrate concentration of the sample of blood according to the measurement information received by said biological component information input device; and a display device operable to display the substrate concentration calculated by said computing device, wherein said memory stores the information regarding the sample collected site and the substrate concentration calculated by said computing device;

said skin contact surface of said cap includes at least two sensors operable to detect contact with skin, said at least two sensors being electrically connected to said sample collection site input device when said cap is detachably engaged with said body of said biological component measurement apparatus;

said sample collection site input device is operable to recognize the sample collection site according to either (i) a number of sensors, (ii) a combination of sensors, or (iii) a number and combination of sensors, which detect contact with the skin; and said sample collection site input device is operable to recognize the sample collection site as a fingertip if only a part of said at least two sensors detect contact with the skin.

13. The biological component measurement apparatus according to claim 12, wherein said sample collection site input device is operable to recognize the sample collection site as any site selected from the group consisting of a palm, a forearm, an upper arm, a thigh, and an abdomen, if all of said at least two sensors detect contact with the skin.

14. The biological component measurement apparatus according to claim 12, further comprising a mealtime input device operable to receive a mealtime or an elapsed time after a meal, wherein:

said memory includes a previously stored correction table or a correction equation for correcting the substrate concentration according to the mealtime or the elapsed time after the meal and the sample collection site; and said computing device is operable to access said previously stored correction table or correction equation, and calculate a corrected substrate concentration according to the mealtime or the elapsed time after the meal and the sample collection site.

15. A biological component measurement apparatus comprising:

a body; and a puncture mechanism operable to puncture skin of a subject for collecting a sample of blood from a sample collection site, said puncture mechanism comprising:

a puncture needle; and a cap, including a skin contact surface having an opening therein, detachably engaged with said body of said biological component measurement apparatus, wherein:

when said skin contact surface of said cap is brought into contact with the skin to be punctured, said puncture needle is operable to move through said opening of said skin contact surface and puncture the skin to produce the sample of blood;

said biological component measurement apparatus further comprises:

a biological component information input device having a biosensor attachment member and a biosensor attached therewith operable to receive the sample of blood and produce measurement information, said biological component input device being operable to receive the measurement information produced by said biosensor;

a sample collection site input device operable to receive information regarding the sample collection site;

a memory device;

a computing device operable to calculate a substrate concentration of the sample of blood according to the measurement information received by said biological component information input device; and a display device operable to display the substrate concentration calculated by said computing device, wherein said memory stores the information regarding the sample collection site and the substrate concentration calculated by said computing device;

said skin contact surface of said cap includes at least two sensors operable to detect contact with skin, said at least two sensors being electrically connected to said sample collection site input device when said cap is detachably engaged with said body of said biological component measurement apparatus;

said sample collection site input device is operable to recognize the sample collection site according to either (i) a number of sensors, (ii) a combination of sensors, or (iii) a number and a combination of sensors, which detect contact with the skin; and said sample collection site input device is operable to recognize the sample collection site as any site selected from the group consisting of a palm, a forearm, an upper arm, a thigh, and an abdomen, if all of said at least two sensors detect contact with the skin.

16. The biological component measurement apparatus according to claim 15 further comprising a mealtime input device operable to receive a mealtime or an elapsed time after a meal, wherein:

said memory includes a previously stored correction table or a correction equation for correcting the substrate concentration according to the mealtime or the elapsed time after the meal and the sample collection site; and said computing device is operable to access said previously stored correction table or correction equation, and calculate a corrected substrate concentration according to the mealtime or the elapsed time after the meal and the sample collection site.

* * * * *

UNITED STATES PATENT AND TRADEMARK OFFICE
CERTIFICATE OF CORRECTION

| | |
|---|---|
| PATENT NO. | : 7,238,160 B2 |
| APPLICATION NO. | : 10/512939 |
| DATED | : July 3, 2007 |
| INVENTOR(S) | : Yuko Taniike et al. |

Page 1 of 1

It is certified that error appears in the above-identified patent and that said Letters Patent is hereby corrected as shown below:

TITLE PAGE
 Section (57), Abstract, Line 9, "surface having an opening" should read --surface includes an opening--.

IN THE CLAIMS

Claim 3
 In column 19, line 30, "device, and" should read --device; and--.
 In column 19, line 52, "said computing" should read --said computing device--.
 In column 19, line 59, "form" should read --from--.

Claim 7
 In column 20, line 11, "collecting" should read --collection--.

Claim 12
 In column 21, line 39, "form" should read --from--.

Signed and Sealed this

Fourth Day of December, 2007

JON W. DUDAS
*Director of the United States Patent and Trademark Office*